United States Patent
Girlando et al.

(10) Patent No.: US 8,860,399 B2
(45) Date of Patent: Oct. 14, 2014

(54) DEVICE FOR MONITORING AT LEAST A PHYSICAL CHARACTERISTIC OF A BUILDING MATERIAL

(75) Inventors: Giovanni Girlando, Catania CT (IT); Alessandro Finocchiaro, Catania CT (IT)

(73) Assignee: STMicroelectronics S.R.L., Agrate Brianza (MB) (IT)

( * ) Notice: Subject to any disclaimer, the term of this patent is extended or adjusted under 35 U.S.C. 154(b) by 261 days.

(21) Appl. No.: 13/242,967

(22) Filed: Sep. 23, 2011

(65) Prior Publication Data

US 2012/0161789 A1  Jun. 28, 2012

(30) Foreign Application Priority Data

Dec. 22, 2010  (IT) .............................. VA2010A0097

(51) Int. Cl.
*G01N 33/38* (2006.01)
*H04Q 9/00* (2006.01)

(52) U.S. Cl.
CPC ............. *H04Q 9/00* (2013.01); *H04Q 2209/40* (2013.01); *G08C 2201/10* (2013.01); *H04Q 2209/88* (2013.01); *G01N 33/38* (2013.01)
USPC .......... 324/71.1; 324/655; 324/601; 307/104; 174/36; 174/102 R; 340/572.1

(58) Field of Classification Search
CPC ....... G01N 33/38; G01N 33/383; H04Q 9/00; H04Q 2209/40; H04Q 2209/88; G01D 21/00–21/02; G08C 2201/10
USPC ......... 324/600, 649, 654, 655, 663, 693, 699, 324/700, 702, 715, 718, 722, 71.1, 71.2, 324/656, 657; 73/86, 786; 702/81, 33–35; 455/41.1, 67.11; 340/540, 665, 505, 340/539.26, 538, 538.16, 870.31, 572.1; 307/104

See application file for complete search history.

(56) References Cited

U.S. PATENT DOCUMENTS

| | | | | |
|---|---|---|---|---|
| 4,845,311 A | * | 7/1989 | Schreiber et al. | 174/36 |
| 4,943,930 A | * | 7/1990 | Radjy | 702/33 |
| 5,703,576 A | * | 12/1997 | Spillman et al. | 340/870.31 |
| 6,529,127 B2 | * | 3/2003 | Townsend et al. | 340/505 |
| 6,950,767 B2 | * | 9/2005 | Yamashita et al. | 702/81 |
| 6,969,807 B1 | * | 11/2005 | Lin et al. | 174/117 F |
| 7,034,660 B2 | * | 4/2006 | Watters et al. | 340/10.41 |
| 7,148,706 B2 | * | 12/2006 | Srinivasan et al. | 324/700 |

(Continued)

FOREIGN PATENT DOCUMENTS

| | | | |
|---|---|---|---|
| GB | 2466269 | 6/2010 | G08C 17/02 |
| GB | 2470225 | 11/2010 | G01N 17/00 |

OTHER PUBLICATIONS

Jin et al., "Reflection and Transmission Properties of Embedded Dipoles and PIFAs inside Concrete at 915MHz" Antennas and Propagation Society International Symposium, 2009, pp. 1-4.

*Primary Examiner* — Huy Q Phan
*Assistant Examiner* — James Split
(74) *Attorney, Agent, or Firm* — Allen, Dyer, Doppelt, Milbrath & Gilchrist, P.A.

(57) ABSTRACT

A monitoring device is for monitoring physical characteristics of a building material. The monitoring device is buried inside a block of the building material, and has a sensor to sense physical characteristics thereof. The sensor transmits a signal representative of the physical characteristics.

16 Claims, 6 Drawing Sheets

(56) References Cited

U.S. PATENT DOCUMENTS

| | | |
|---|---|---|
| 7,180,404 B2 * | 2/2007 | Kunerth et al. ............ 340/10.41 |
| 7,347,101 B2 * | 3/2008 | Thomson et al. ............... 73/773 |
| 7,551,058 B1 * | 6/2009 | Johnson et al. ........... 340/10.41 |
| 7,637,166 B2 * | 12/2009 | Hecht et al. ..................... 73/803 |
| 7,673,501 B2 * | 3/2010 | Holyoake ......................... 73/73 |
| 7,860,680 B2 * | 12/2010 | Arms et al. .................. 702/127 |
| 7,986,218 B2 * | 7/2011 | Watters et al. ............. 340/10.41 |
| 8,091,432 B2 * | 1/2012 | Hecht et al. ..................... 73/803 |
| 8,635,916 B1 * | 1/2014 | Loverich et al. ................ 73/768 |
| 2004/0153270 A1 | 8/2004 | Yamashita et al. ............. 702/81 |
| 2005/0204825 A1 | 9/2005 | Kunerth et al. ................. 73/786 |
| 2009/0033467 A1 | 2/2009 | Finocchiaro et al. ........... 340/10 |
| 2010/0190435 A1 * | 7/2010 | Cook et al. .................... 455/41.1 |
| 2011/0199107 A1 * | 8/2011 | Adamian et al. ......... 324/750.02 |
| 2013/0106447 A1 * | 5/2013 | Bridges et al. ................. 324/700 |

* cited by examiner

DEVICE FOR MONITORING AT LEAST A PHYSICAL CHARACTERISTIC OF A BUILDING MATERIAL

FIELD OF THE INVENTION

This invention relates in general to monitoring circuitry, and, more particularly, to a monitoring device for a physical characteristic of a building material adapted to be buried inside a building material.

BACKGROUND OF THE INVENTION

The strategy for implementing damage detection and the characterization of mechanical structures is commonly called Structural Health Monitoring (SHM). Damages are defined as modifications of the material and/or of the geometrical properties of a structural system, comprising modifications of boundary conditions and connections of the system, that worsen performances of the system. The SHM process implies the observation of the mechanical system over the time using periodically: measurements of dynamic responses coming from an array of sensors, extraction of data of damage characteristics sensed from these measurements, and statistical analysis of these data of characteristics for determining the present health state of the system (also called structural analysis).

The (periodically updated) output of this process is an information about the capacitance of the structure of carrying out its function, considering the unavoidable aging and of degradation in working environments. After extreme events, such as earthquakes or explosions, the SHM is used for a quick screening of the conditions of the structure for providing, almost in real time, reliable information about the integrity of the structure itself.

Nowadays, SHM systems use sensors located outside the surfaces to be controlled. For example, in bridges a number of sensors are used (anemometers for calculating the wind speed, accelerometers, extensometers, motion transducers, temperature sensors, sensors for detecting motion of weights, etc.), which are placed on the external surfaces of beams, ropes or pillars, in order to estimate the effects of loads on the bridge, evaluate the weakening of the bridge, and foresee the probable evolution of the bridge and its expected lifetime.

There are technical reasons that hinder the realization of cost efficient SHM with sensors buried in the same structures to be monitored. In particular, any sensor (of pressure, moisture, temperature, etc.) inside a block of reinforced concrete should be connected to an antenna or to a conductor for communicating outside the block itself the sensed measurements.

Let us consider for example a sensor, buried in a block of concrete, that should communicate to the outside through an antenna buried in the same block. The block of reinforced concrete may cause an attenuation that could range between 0.5 and 1 dB per cm of thickness. See Xiaohua Jin, M. Ali "Reflection and Transmission Properties of Embedded Dipoles and PIFAs inside Concrete at 915 MHz" Antennas and Propagation Society International Symposium, 2009, Print ISBN: 978-1-4244-3647-7. This imposes, at least, a maximum communication distance between the buried sensor (supposedly not supplied by a local battery) and an external sensor, fixed by an energy budget.

Moreover, electromagnetic characteristics of reinforced concrete (different from those of air) cause a reduction of the resonance frequency of the antenna (antenna detuning), that should be taken into consideration while designing. Finally, the presence of metal structures close to the antenna causes interferences that could jeopardize reliability of communications towards the outside.

If a battery connected to the sensor was used instead, there would be time limits of use of the sensor fixed by the battery charge.

The antenna and the radio part of present SHM sensors are physically connected to each other through bond-wire (or bump). This causes reliability problems because inside blocks of pre-compressed reinforced concrete in steady-state conditions (attained after about 1 month), there are pressures of the order of hundreds of atmospheres that make this physical connection between the antenna and the radio part of the SHM sensor very difficult. The poor reliability of this physical connection between antenna and radio part of the SHM sensor is the reason that explains why no sensor is simply connected to the outside through an electric wire (wired connection).

SUMMARY OF THE INVENTION

A monitoring device for a physical characteristic of a building material, adapted to be buried inside the same building material and that brilliantly overcomes limitations of known devices, has been devised.

The monitoring device comprises a sensor of the physical characteristic to be monitored, that has an inductor and a circuit adapted to provide an internal supply voltage when the switch is immersed in a variable magnetic field and to transmit a signal representative of the sensed physical characteristic, and for a wireless power supply of the sensor having a resonant L-C series circuit buried into a dielectric layer. The sensor is installed on the dielectric layer and has its inductor magnetically coupled to the inductor of the resonant circuit. The power supplier further has two current terminals that come out of the dielectric layer and that are connectable to a reading circuit of data transmitted by the sensor. The device is adapted to be buried into a block of building material such that the current terminals of the wireless supply come out of the block.

DETAILED DESCRIPTION OF THE PREFERRED EMBODIMENTS

The monitoring device shows advantages of a wired connection while avoiding, at the same time, physical connection between the radio part of the SHM sensor and the "communication circuitry" toward outside of the mechanical structure. Hereinafter reference is made to the "communication circuitry" and not to an antenna for the reasons that will be explained herein below.

Figure 1:
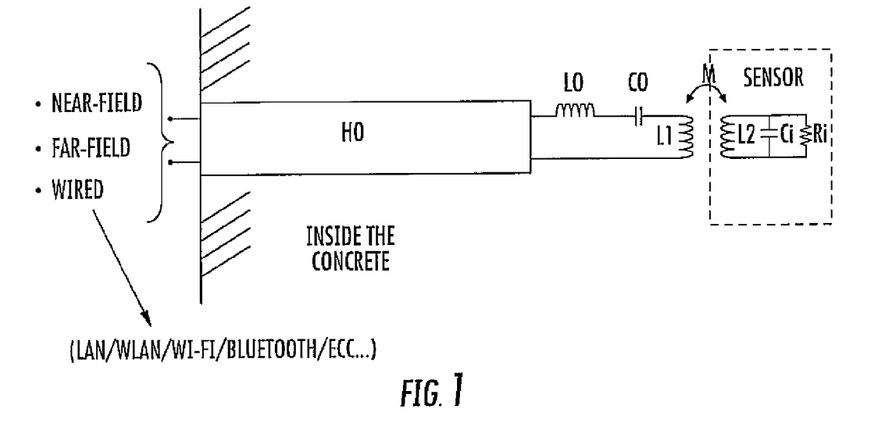
FIG. 1 is an electric scheme of the monitoring device.

A basic scheme of the proposed device is depicted in FIG. 1.

Figure 2:
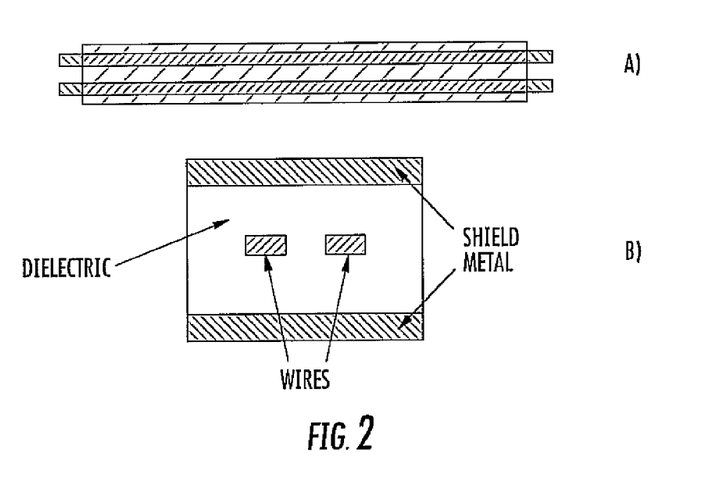
FIG. 2 shows: a) a top view of the shielded strip of an embodiment of the device of FIG. 1; b) a transversal section of the shielded strip of an embodiment of the device of FIG. 1.
Figure 3:
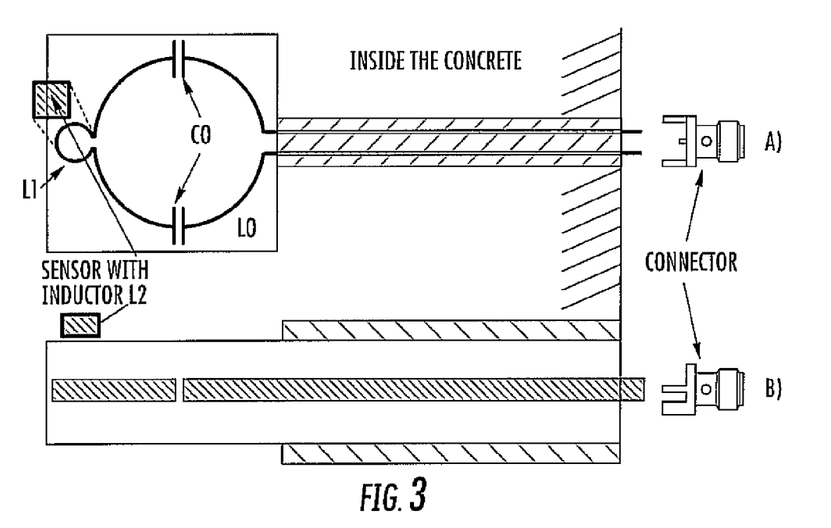
FIG. 3 shows: a) a top view of an embodiment of the device of FIG. 1; b) a side section of an embodiment of the device of FIG. 1.

Inside the block of building material, that may be reinforced concrete, is buried a wireless power supply device having a L-C resonant circuit buried in a dielectric layer, optionally but not necessarily shielded by a double metal layer, that realizes a physical connection (WIRED) between the outside and the interface with the sensor, as shown in FIG. 2. This structure, that may be rigid or flexible, is hereinafter called "shielded strip".

The "shielded strip", that prevents the use of the antenna inside the mechanical structure, helps eliminate power losses between antenna and the external apparatus to the mechanical structure due to the reinforced concrete, and further avoids interference problems between antenna and metal structures (reinforcement) in the same block of reinforced concrete.

Moreover, the design/fabrication of the shielded strip does not depend upon the material in which it will be buried. Moreover, this makes the device almost immediately operative because communications between the shielded strip and the sensor do not depend on the mechanical properties and on the electromagnetic parameters (electric conductivity and dielectric constant) of the material in which it will be buried. By contrast, with the known devices that use an antenna buried in a block of reinforced concrete, it is helpful to consider the issue of the antenna detuning and to wait at least 28-30 days in order to let the mechanical properties and the electromagnetic parameters of the reinforced concrete attain a steady state condition before using in a reliable manner the monitoring device.

Close to the sensor "hybrid transformer", A. Finocchiaro, et al, "RF identification device with near-field-coupled antenna" US patent application number US2009033467, is realized between a primary inductor L1 located on the shielded strip and a secondary inductor L2 that will be interfaced with the radio part of the sensor. This hybrid transformer, that establishes a magnetic coupling between a sensor and a shielded strip, avoids the issue of realizing a bonding.

Moreover, in order to increase the effectiveness of the magnetic coupling in the hybrid transformer, it is helpful to increase both the current through the primary inductor L1 as well as the voltage generated on the secondary inductor L2. For the primary circuit, this is obtained by realizing a series resonance at the working frequency ω between the inductor L1 and the added capacitor C0, that is:

$$\omega^2 L1 C0 = 1$$

for the secondary circuit this is obtained by realizing a parallel resonance at the working frequency ω between the inductor L2 and the capacitor Ci, that is:

$$\omega^2 L2 Ci = 1$$

wherein Ci is given by the equivalent input capacitance of the integrated circuit plus an additional contribution adapted to obtain said resonance. In general, if it is difficult to realize the capacitance C0 (high value, losses, precision or fluctuations due to variations of the pressure to which is subjected, etc.) it is possible to add a further inductor L0, thus realizing the following condition:

$$\omega^2 (L0+L1) C0 = 1$$

in order to reduce the value of C0 and thus make it compatible with the materials and realization techniques of the same shielded strip. The inductor L0 and the capacitor C0 may be realized in many different ways, as shown in figures from 3 to 11.

Figure 4:
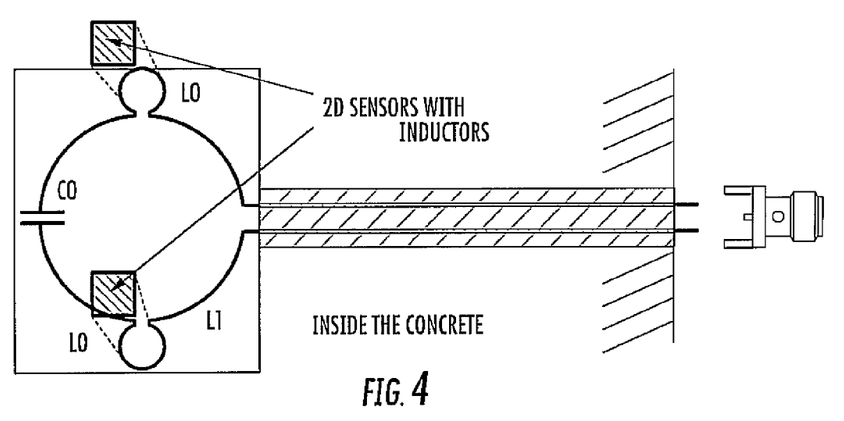
FIG. 4 shows another embodiment of the monitoring device.
Figure 5:
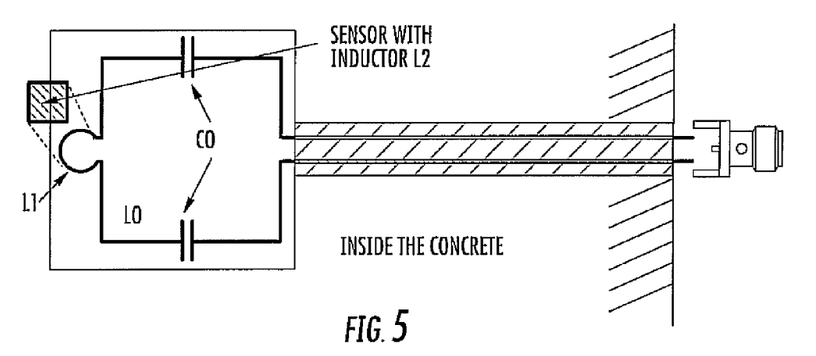
FIG. 5 shows yet another embodiment of the monitoring device.
Figure 6:
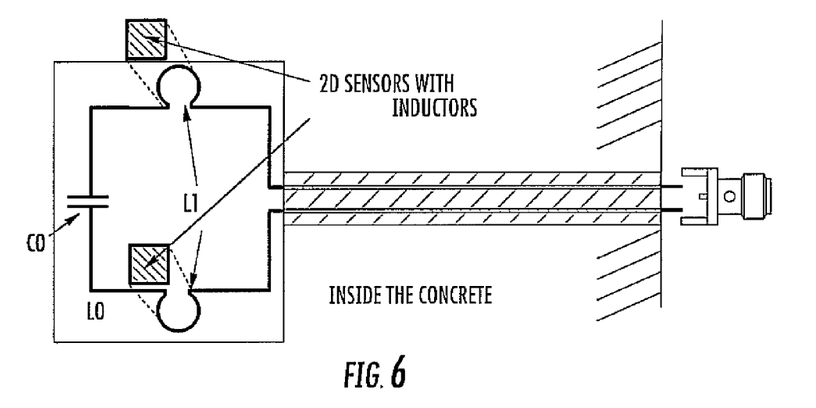
FIG. 6 shows yet another embodiment of the monitoring device.
Figures 7, 8:
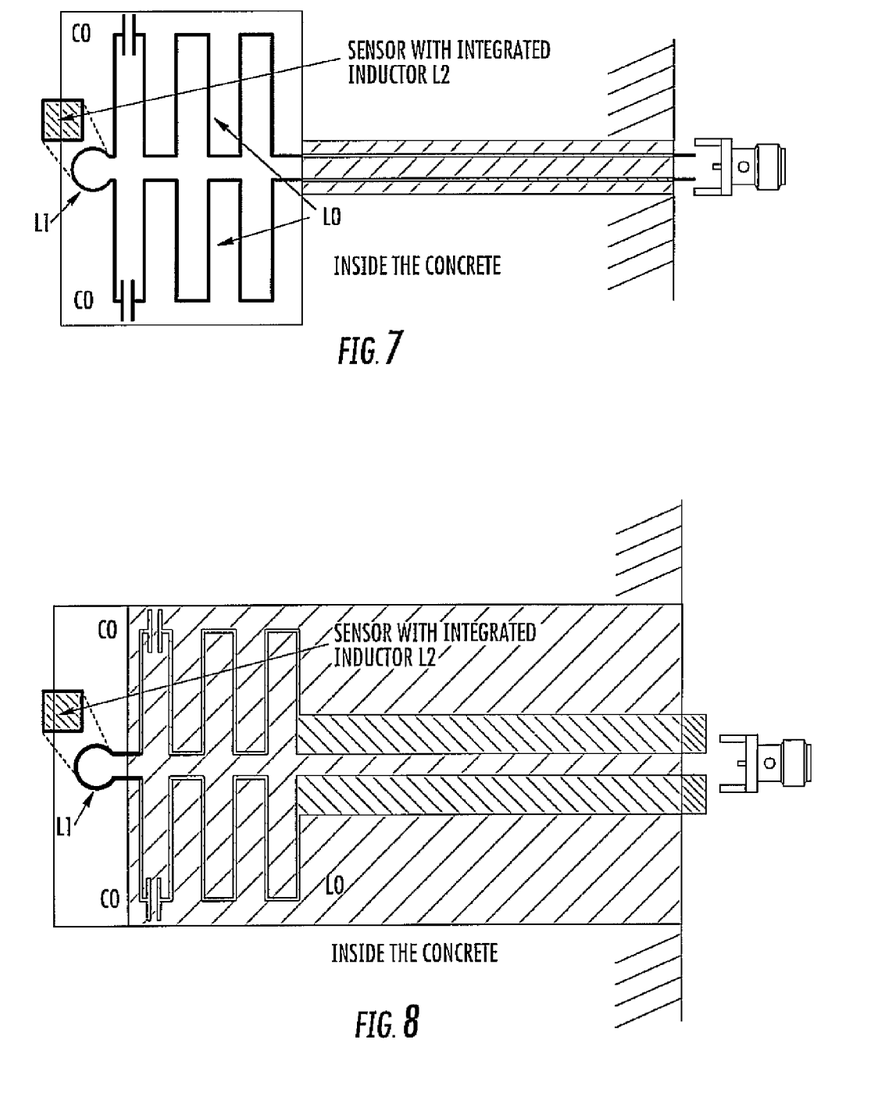
FIG. 7 shows yet another embodiment of the monitoring device.
FIG. 8 shows yet another embodiment of the monitoring device.
Figure 9:
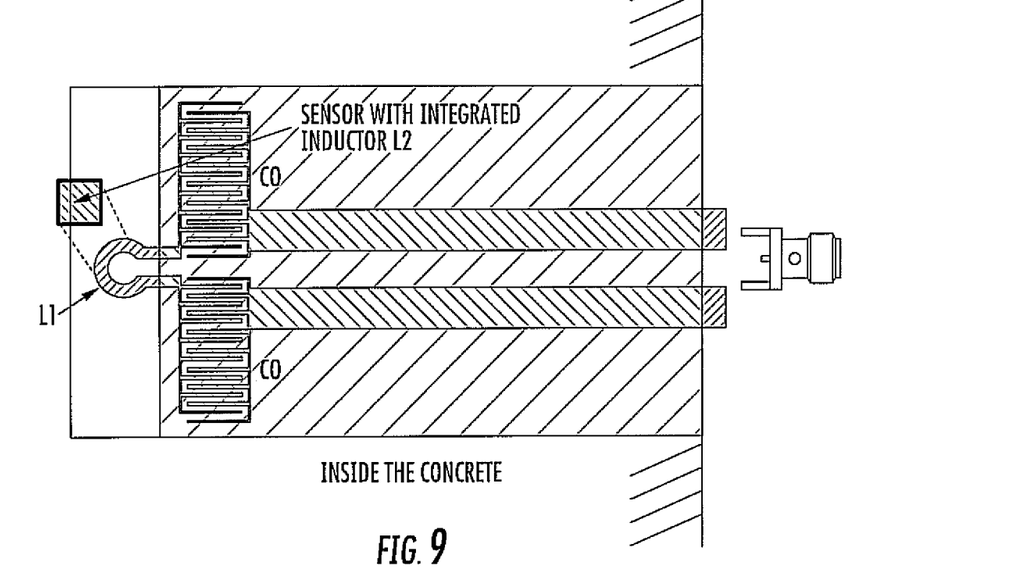
FIG. 9 shows yet another embodiment of the monitoring device.
Figure 10:
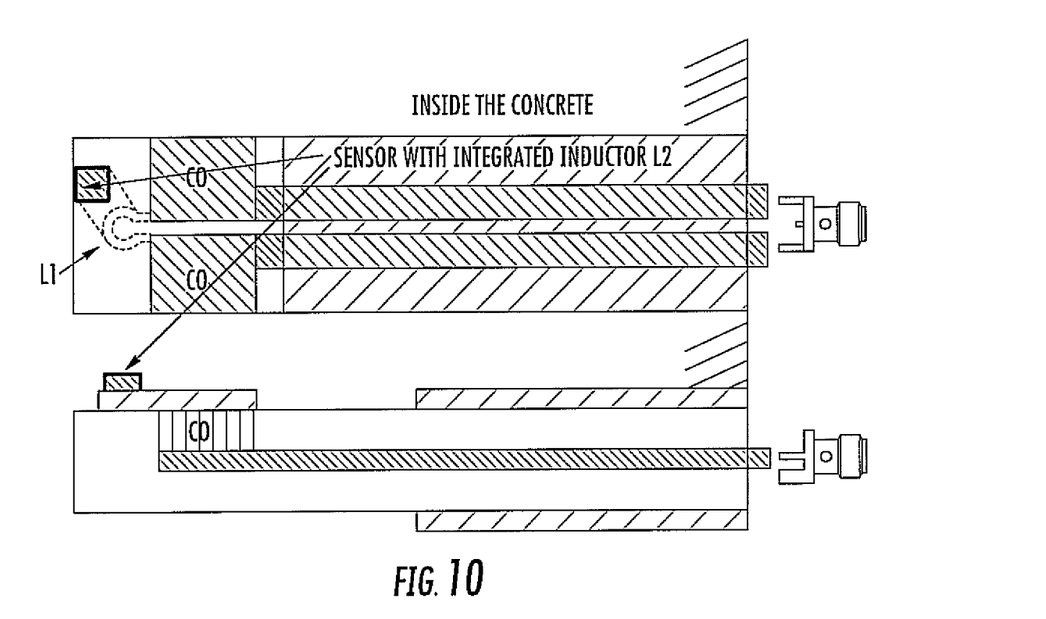
FIG. 10 shows yet another embodiment of the monitoring device.
Figure 11:
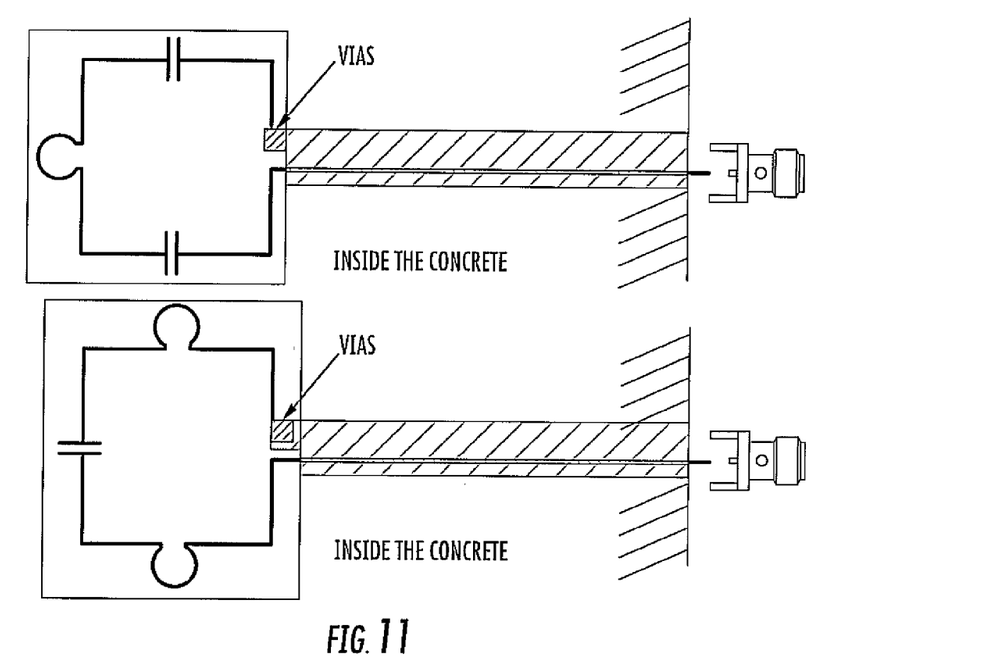
FIG. 11 shows yet other embodiments of the monitoring device.

It is possible to realize a rigid or flexible shielded strip as long as desired, because its losses are those typical of shielded conductors (fractions of dB/m compared with dB/cm of reinforced concrete). This device practically does not impose any limits to the distance from the surface at which the sensor may be buried, because it is not affected by the typical problems of power budget that affect known devices in which the sensor (or sensors) is powered using an antenna inside the block of concrete. Moreover, with the structure "shielded", it is possible to place its sensors close to or at least advantageously anchored to the steel reinforcing rods inside the block of reinforced concrete. If two or three sensors are positioned along the directions of as many orthogonal axes of the shielded strip, as schematically shown in FIGS. 4 and 6 for example, it is possible to realize a local monitoring in two or three dimensions. Indeed, in the present embodiment there are neither power constraints nor interference between antennas when positioning close among them three or more sensors. The data management could in this case be carried out by using appropriate anti-superposition algorithms similar to those used for RFID systems.

Figure 12:
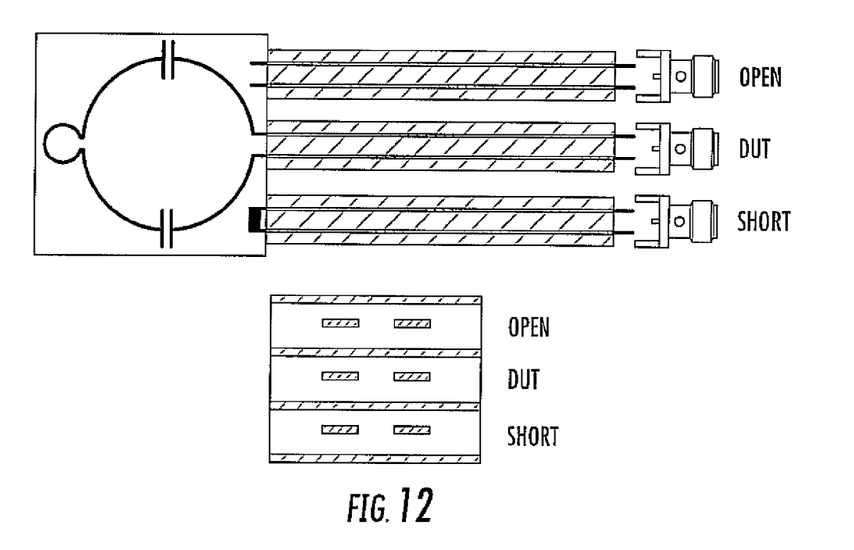
FIG. 12 shows yet another embodiment of the monitoring device with a de-embedding structure and the related transversal section.

The proposed structure allows easy execution of the calibration phase of the shielded strip. Indeed, by implementing the structure composed of three shielded strips depicted in FIG. 12, it is possible to carry out a "de-embedding" of the same shielded strip, that is to remove systematic measurement errors of the properties of the building material introduced by the same shielded strip. This makes the characterization of the resonance series network including the components L0 and C0 (and eventually L1) of FIG. 1 easier.

That which is claimed is:

1. A monitoring device for at least one physical characteristic of a building material, the monitoring device buried inside a block of the building material and comprising:

a sensor buried inside the block of the building material and configured to sense the at least one physical characteristic and comprising a secondary inductor and a circuit coupled thereto, said circuit configured to generate an internal supply voltage for said sensor when immersed in a variable electromagnetic field and to transmit a signal representative of the physical characteristic; and a wireless power supplier buried inside the block of the building material and configured to generate the variable electromagnetic field for said sensor and comprising a dielectric layer and a resonant L-C circuit therein, said resonant L-C circuit comprising a primary inductor configured to be magnetically coupled to said secondary inductor of said sensor, said wireless power supplier further comprising two current terminals extending from said dielectric layer to external the block of the building material so as to be coupleable to an external reading circuit for the signal;

said sensor being adjacent said dielectric layer so as to magnetically couple said primary inductor and said secondary inductor.

2. The monitoring device of claim 1, wherein said wireless power supplier further comprises electromagnetic shielding metallic layers on said dielectric layer; and further comprising adjacent electric connection lines coupling said resonant L-C circuit and said two current terminals of said wireless power supplier.

3. The monitoring device of claim 2, wherein the electromagnetic shielding metallic layers on said dielectric layer are adjacent said resonant L-C circuit except said primary inductor.

4. The monitoring device of claim 2, further comprising additional dielectric layers on opposing sides of said electromagnetic shielding metallic layers on said dielectric layer; and an opened bifilar line and a shorted bifilar line buried in respective additional dielectric layers, having respective shielding metallic layers, and forming a sandwich structure with said dielectric layer in which said electric connection lines are buried.

5. The monitoring device of claim 2, wherein said secondary inductor and said circuit are integrated together in an integrated circuit.

6. A monitoring device for a physical characteristic of a building material comprising:
a sensor buried inside the building material and configured to sense the physical characteristic and comprising a circuit configured to generate an internal supply voltage based upon a variable field and to transmit a signal representative of the physical characteristic; and
a wireless power supplier buried inside the building material and configured to generate the variable field for said sensor and comprising a resonant L-C circuit, and external terminals that extend external the building material so as to be coupleable to an external reading circuit for the signal.

7. The monitoring device of claim 6, wherein said wireless power supplier further comprises electromagnetic shielding metallic layers; and further comprising adjacent electric connection lines coupling said resonant L-C circuit and said external terminals of the wireless power supplier.

8. The monitoring device of claim 7, wherein the electromagnetic shielding metallic layers are adjacent said resonant L-C circuit except said primary inductor.

9. The monitoring device of claim 7, further comprising additional dielectric layers on opposing sides of said electromagnetic shielding metallic layers on said dielectric layer; and an opened bifilar line and a shorted bifilar line buried in respective additional dielectric layers and having respective shielding metallic layers.

10. A method of making a monitoring device for at least one physical characteristic of a building material, the monitoring device buried inside a block of the building material and comprising:
configuring a sensor buried inside the block of the building material to sense the at least one physical characteristic, the sensor comprising a secondary inductor and a circuit coupled thereto, and configuring the circuit to generate an internal supply voltage for the sensor when immersed in a variable electromagnetic field and to transmit a signal representative of the physical characteristic; and
configuring a wireless power supplier buried inside the block of the building material to generate a variable electromagnetic field for the sensor, the wireless power supplier comprising a resonant L-C circuit in a dielectric layer, the resonant L-C circuit having a primary inductor configured to be magnetically coupled to the secondary inductor of the sensor, the wireless power supplier further comprising two current terminals extending from the dielectric layer to external the block of the building material so as to be coupleable to an external reading circuit for the signal, the sensor being adjacent the dielectric layer so as to magnetically couple the primary inductor and the secondary inductor.

11. The method of claim 10, wherein the wireless power supplier further comprises electromagnetic shielding metallic layers deposited on the dielectric layer and adjacent electric connection lines coupling the resonant L-C circuit and the two current terminals of the wireless power supplier.

12. The method of claim 11, wherein the electromagnetic shielding metallic layers on the dielectric layer are adjacent the resonant L-C circuit except the primary inductor.

13. The method of claim 11, further comprising additional dielectric layers on opposing sides of the electromagnetic shielding metallic layers on the dielectric layer; and burying an opened bifilar line and a shorted bifilar line in respective additional dielectric layers, the opened bifilar line and the shorted bifilar line having respective shielding metallic layers, and forming a sandwich structure with the dielectric layer in which the electric connection lines are buried.

14. The method of claim 10, wherein the secondary inductor and the circuit are integrated together in an integrated circuit.

15. A method of making a monitoring device for at least one physical characteristic of a building material comprising:
configuring a sensor buried inside the building material and configured to sense the physical characteristic, the sensor comprising a circuit, and configuring the circuit to generate an internal supply voltage when immersed in a variable field and to transmit a signal representative of the physical characteristic; and
configuring a wireless power supplier buried inside the building material to generate the variable field, the wireless power supplier comprising a resonant L-C circuit for the sensor, and external terminals that extend external the building material so as to be coupleable to an external reading circuit for the signal.

16. The method of claim 15, wherein the wireless power supplier further comprises electromagnetic shielding metallic layers deposited on the dielectric layer and adjacent electric connection lines coupling the resonant L-C circuit and the two current terminals of the wireless power supplier; and further comprising additional dielectric layers on opposing sides of the electromagnetic shielding metallic layers on the dielectric layer; and burying an opened bifilar line and a shorted bifilar line in respective additional dielectric layers, the opened bifilar line and the shorted bifilar line having respective shielding metallic layers.

* * * * *